(12) United States Patent
Hwang (10) Patent No.: US 8,949,060 B2
(45) Date of Patent: Feb. 3, 2015

(54) INSPECTION METHOD

(75) Inventor: Bong-Ha Hwang, Seoul (KR)

(73) Assignee: Koh Young Technology Inc., Seoul (KR)

( * ) Notice: Subject to any disclaimer, the term of this patent is extended or adjusted under 35 U.S.C. 154(b) by 648 days.

(21) Appl. No.: 13/295,757

(22) Filed: Nov. 14, 2011

(65) Prior Publication Data

US 2012/0123719 A1  May 17, 2012

(51) Int. Cl.
*G01N 21/88* (2006.01)
*G01N 21/956* (2006.01)
(Continued)

(52) U.S. Cl.
CPC ............ *G01N 11/24* (2013.01); *G01N 21/8851* (2013.01); *G06F 19/00* (2013.01); *G06F 17/40* (2013.01); *G01N 21/956* (2013.01)
USPC ................... 702/105; 73/1.01; 702/1; 702/85; 702/127; 702/182; 702/189

(58) Field of Classification Search
CPC ............ G01B 9/00; G01B 9/08; G01B 11/00; G01B 11/24; G01B 21/00; G01D 7/00; G01D 9/00; G01D 21/00; G01N 21/00; G01N 21/84; G01N 21/88; G01N 21/8851; G01N 21/95; G01N 21/956; G01N 2021/00; G01N 2021/84; G01N 2021/88; G01N 2021/8851; G01N 2021/95; G01N 2021/956; G01N 2021/95607; G01N 2021/95638; G06F 11/00; G06F 11/30; G06F 11/32; G06F 11/34; G06F 15/00; G06F 15/16; G06F 17/00; G06F 17/10; G06F 17/40; G06F 19/00; G01G 9/00
USPC .............. 73/1.01, 432.1, 865.8, 865.9, 866.3; 324/500, 537, 763.01, 763.02; 356/237.1, 237.2, 237.3, 237.4, 237.5; 382/100, 141, 145, 147, 149, 150; 702/1, 85, 105, 127, 182, 187, 189; 708/100, 105, 200; 250/200, 252.1, 250/306, 559.01, 559.04, 559.5, 559.07, 250/559.08, 559.1, 559.19, 559.2, 559.39
See application file for complete search history.

(56) References Cited

U.S. PATENT DOCUMENTS 3,340,400 A * 9/1967 Quittner .................... 250/559.46
3,388,631 A * 6/1968 Glowa ........................ 356/390
(Continued)

FOREIGN PATENT DOCUMENTS

CN  1263270  8/2000
CN  1504742  6/2004
(Continued)

*Primary Examiner* — Edward Cosimano
(74) *Attorney, Agent, or Firm* — Kile Park Reed & Houtteman PLLC (57) ABSTRACT

In order to set an inspection area in an inspection apparatus for inspecting a board, a plurality of measurement areas are set on a board, and then reference data and measurement data of at least one adjacent measurement area that is adjacent to a target measurement area for inspecting a measurement target, among the measurement areas, are acquired. Thereafter, at least one feature object is extracted from the adjacent measurement area. Then, a distortion degree is acquired by comparing reference data and measurement data corresponding to the feature object with each other, and thereafter the distortion degree is compensated for, to set an inspection area in the target measurement area. Thus, a conversion relation between the reference data and the measurement data may be correctly acquired, and an inspection area, in which distortion is compensated for, may be correctly set.

15 Claims, 7 Drawing Sheets

(51) Int. Cl.
   *G06F 17/40*   (2006.01)
   *G06F 19/00*   (2011.01)

(56) References Cited

U.S. PATENT DOCUMENTS

| | | | |
|---|---|---|---|
| 3,391,599 A * | 7/1968 | Fleisher et al. | 356/511 |
| 4,056,716 A * | 11/1977 | Baxter et al. | 382/148 |
| 5,506,793 A * | 4/1996 | Straayer et al. | 702/85 |
| 5,774,574 A | 6/1998 | Hoki | |
| 8,260,030 B2 * | 9/2012 | Kim et al. | 382/141 |
| 8,437,533 B2 * | 5/2013 | Kim et al. | 382/141 |
| 2010/0092041 A1 * | 4/2010 | Kim et al. | 382/106 |
| 2010/0246931 A1 * | 9/2010 | Kim et al. | 382/141 |
| 2011/0002527 A1 * | 1/2011 | Jeong et al. | 382/141 |
| 2012/0123719 A1 * | 5/2012 | Hwang | 702/85 |
| 2012/0128231 A1 * | 5/2012 | Hwang | 382/147 |
| 2012/0130666 A1 * | 5/2012 | Cho et al. | 702/87 |
| 2013/0215262 A1 * | 8/2013 | Jeong et al. | 348/126 |
| 2013/0229509 A1 * | 9/2013 | Kim et al. | 348/86 |

FOREIGN PATENT DOCUMENTS

| | | |
|---|---|---|
| CN | 1728160 | 2/2006 |
| CN | 1746667 | 3/2006 |
| CN | 101852745 | 10/2010 |
| KR | 1020080002044 A | 1/2008 |
| KR | 10-2010-0113093 | 10/2010 |
| KR | 1020100108877 A | 10/2010 |

* cited by examiner

INSPECTION METHOD

CROSS REFERENCE TO RELATED APPLICATION

This application claims priority from and the benefit of Korean Patent Applications No. 2010-113093 filed on Nov. 15, 2010, which is hereby incorporated by reference for all purposes as if fully set forth herein.

BACKGROUND OF THE INVENTION

1. Field of the Invention

Exemplary embodiments of the present invention relate to an inspection method. More particularly, exemplary embodiments of the present invention relate to an inspection method for a measurement target by using a shape measurement apparatus.

2. Discussion of the Background

Generally, at least one printed circuit board (PCB) is employed in an electronic device, and various circuit elements such as a circuit pattern, a connection pad part, a driver chip electrically connected to the connection pad part, etc. are mounted on the PCB.

A shape measurement apparatus is typically used to check whether the various circuit elements are formed or configured good or not on the printed circuit board.

In a conventional shape measurement apparatus, a predetermined inspection area is set to inspect whether circuit elements are formed good or not in the inspection area. In a conventional method of setting an inspection area, an area, in which circuit elements are theoretically located, is simply set as an inspection area.

When the inspection area is set at a correct location, a measurement of a desired circuit element is performed well. However, in a measurement target such as a PCB, distortion such as warpage, contortion, etc. of a base board may be generated. Thus, in the conventional method of setting an inspection area, the inspection area is not correctly set at a desired location, and a location corresponding to an image acquired in a camera of an image capturing part is a little different from a location where a circuit element actually exists.

Thus, an inspection area is required to set to compensate for the distortion of the measurement target.

SUMMARY OF THE INVENTION

Exemplary embodiments of the present invention provide an inspection apparatus capable of setting an inspection area in which distortion of a board is compensated for, and correctly setting an inspection area by acquiring a conversion relation between reference data and measurement data, even though there is no shape information or insufficient shape information for establishing a feature object in a target measurement area on a board.

Additional features of the invention will be set forth in the description which follows, and in part will be apparent from the description, or may be learned by practice of the invention.

An exemplary embodiment of the present invention discloses an inspection method. The inspection method includes setting a plurality of measurement areas on a board, acquiring reference data and measurement data of at least one adjacent measurement area that is adjacent to a target measurement area for inspecting a measurement target, among the measurement areas, extracting at least one feature object from the adjacent measurement area, acquiring a distortion degree by comparing reference data and measurement data corresponding to the feature object with each other, and compensating for the distortion degree to set an inspection area in the target measurement area.

Extracting at least one feature object in the adjacent measurement area may include establishing a reference type and a reference number of the feature object, and extracting the feature object corresponding to the reference type from the adjacent measurement area, in case that the number of the feature object extracted from the target measurement area is smaller than the reference number. The adjacent measurement area may be plural. Before extracting the feature object corresponding to the reference type from the adjacent measurement area, extracting at least one feature object from the adjacent measurement area further includes selecting the adjacent measurement area for extracting the feature object among the plurality of adjacent measurement areas.

In an exemplary embodiment, before extracting at least one feature object from the adjacent measurement area, the inspection method further includes establishing the feature object for each measurement area, checking whether the number of the established feature object is smaller than a reference number or not, for each measurement area, and selecting the adjacent measurement area for extracting the feature object for the measurement area in which the number of the established feature object is smaller than the reference number.

In an exemplary embodiment, the feature object may be extracted from a specific adjacent measurement area in which the measurement data is acquired before the measurement data of the target measurement area is acquired.

In an exemplary embodiment, extracting at least one feature object from the adjacent measurement area may include establishing a reference type and a reference number of the feature object, enlarging the target measurement area by a predetermined area, extracting the feature object corresponding to the reference type in the enlarged area, and repeating the step of enlarging the target measurement area by a predetermined area, and the step of extracting the feature object corresponding to the reference type in the enlarged area, in case that the number of the extracted feature object is smaller than the reference number. Enlarging the target measurement area by a predetermined area may be performed by extracting the feature object corresponding to the reference type in an intersection area between the enlarged area and at least one selected adjacent measurement area. Before enlarging the target measurement area by a predetermined area, extracting at least one feature object from the adjacent measurement area may further include extracting the feature object corresponding to the reference type in the target measurement area, and enlarging the target measurement area by a predetermined area may be performed, in case that the number of the feature object extracted from the target measurement area is smaller than the reference number.

In an exemplary embodiment, the extracted feature object may be plural. A greater weighted value may be given to the feature object as a distance between the feature object and the target measurement area is nearer, and the distortion degree may be acquired by comparing the reference data and the measurement data corresponding to the feature object selected based on the weighted value with each other. The distance may be measured from at least one of a boundary line of the target measurement area, a central point of the target measurement area and a central point of the measurement target.

In an exemplary embodiment, the extracted feature object may be plural. A greater score may be given to the feature object as a shape difference between the reference data and the measurement data corresponding to the feature object is smaller, and the distortion degree may be acquired by comparing the reference data and the measurement data corresponding to the feature object selected based on the score with each other.

In an exemplary embodiment, the extracted feature object may be plural. A greater weighted value may be given to the feature object as a distance between the feature object and the target measurement area is nearer. A greater score may be given to the feature object as a shape difference between the reference data and the measurement data corresponding to the feature object is smaller. The distortion degree may be acquired by comparing the reference data and the measurement data corresponding to the feature object selected based on at least one of the weighted value and the score with each other.

In an exemplary embodiment, the adjacent measurement area may be plural, and the extracted feature object may be plural. The feature objects may be evenly extracted for the plurality of adjacent measurement areas.

Another exemplary embodiment of the present invention discloses an inspection method. The inspection method includes setting a plurality of measurement areas on a board, acquiring reference data and measurement data of at least one adjacent measurement area that is adjacent to a target measurement area for inspecting a measurement target, among the measurement areas, extracting at least one feature block having a block unit from the adjacent measurement area, acquiring a distortion degree by comparing reference data and measurement data corresponding to the feature block with each other, and compensating for the distortion degree to set an inspection area in the target measurement area.

In an exemplary embodiment, the extracted feature block may be plural. The distortion degree may be acquired as a quantified conversion formula between the reference data and the measurement data. The quantified conversion formula may be determined by using at least one of a location change, a slope change, a size change and a transformation degree, which are acquired by comparing the reference data and the measurement data corresponding to the plurality of feature objects with each other.

According to the present invention, in case that there is no shape information or few shape information for establishing a feature object in the target measurement area on a board, a feature object is additionally established in an adjacent measurement area to thereby more correctly acquire a conversion relation between reference data and measurement data, and set an inspection area by compensating for distortion of measurement data with the conversion relation.

In addition, in case of establishing a feature block including a specific shape by a block unit as a feature object, since it may occur sometimes that there is insufficient shape information selectable as a feature object, a feature object in an adjacent measurement area may be used, as described above, to acquire the sufficient number of feature objects.

In addition, in case that weighted value is established for feature objects in a target measurement area and an adjacent measurement area, a conversion relation comparatively correct may be acquired. In addition, in case that feature objects are evenly established for a plurality of adjacent measurement areas, a conversion relation comparatively correct may be acquired.

In addition, an error may be prevented, which may occur due to change of an inspection area, which is incurred from location changes of a pad and a component according to warpage or contortion of a board, and an inspection area may be more correctly set.

In addition, a work such as a failure inspection in a component may be performed based on an inspection area that is set as described above, it may be correctly judged whether the board is good or bad.

In addition, information of a measurement target existing in a measurement area may be correctly measured by using the measurement area that is set as described above.

In addition, contortion between reference data and measurement data is compensated for, and thus areas of a pad, a component, a pattern, a silk, etc. existing in the measurement data may be more correctly predicted from the reference data.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 1:
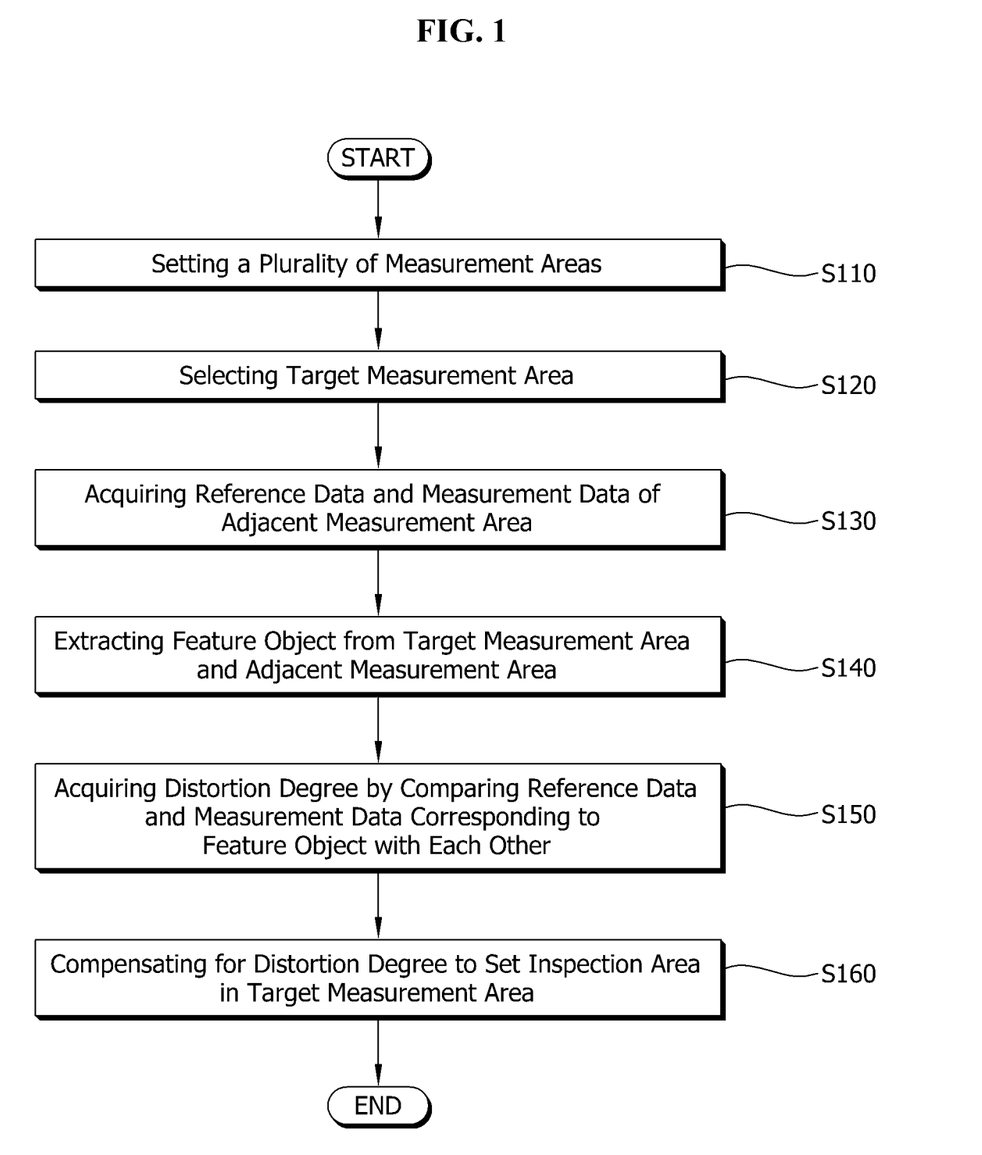
FIG. 1 is a flow chart illustrating an inspection method according to an exemplary embodiment of the present invention.
Figure 2:
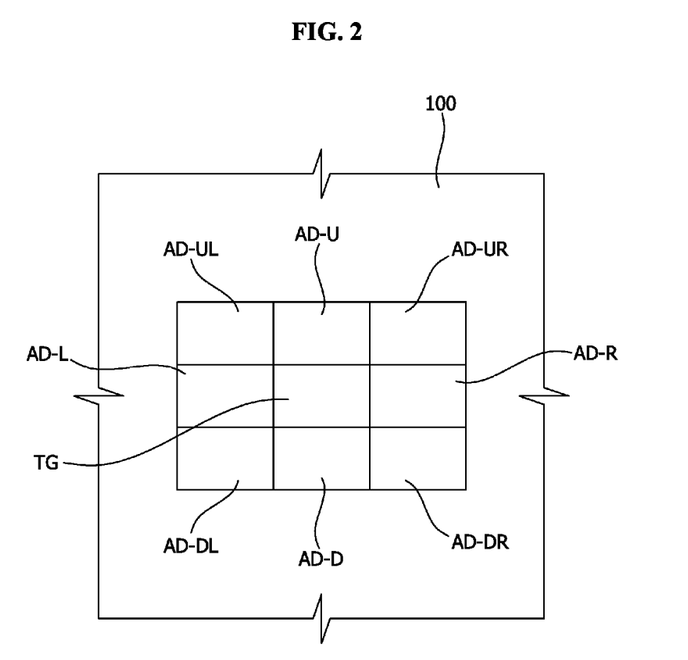
FIG. 2 is a plan view illustrating the inspection method shown in FIG. 1.

FIG. 1 is a flow chart illustrating an inspection method according to an exemplary embodiment of the present invention. FIG. 2 is a plan view illustrating the inspection method shown in FIG. 1.

Referring to FIGS. 1 and 2, in order to set an inspection area in which distortion is compensated for according to an exemplary embodiment of the present invention, firstly a plurality of measurement areas is set on the board 100 in step of S110.

The measurement areas indicates a predetermined area that is set on the board 100 so as to inspect whether the board 100 is bad or not, and may be defined, for example, based on a "field of view" of a camera installed in an inspection apparatus such as a three dimensional shape measurement apparatus.

Then, a target measurement area corresponding to an area desired for inspecting a measurement target is selected as an inspection area in step of S120.

According as the target measurement area is selected, there exists an adjacent measurement area adjacent to the target measurement area. The adjacent measurement area is variable according to a shape and a location of the measurement areas. In case that the measurement areas has a rectangular shape, there exists at least three adjacent measurement areas, and there may exist eight adjacent measurement areas. In FIG. 2, the target measurement area TG is located at the middle of the board 100, and an example is shown to illustrate the locations of eight adjacent measurement areas AD-U, AD-D, AD-L, AD-R, AD-UL, AD-DL, AD-UR and AD-DR adjacent to the upper side, the lower side, the left side, the right side, the upper left side, the lower left side, the upper right side and the lower right side, respectively, of the target measurement area TG. The four adjacent measurement areas AD-UL, AD-DL, AD-UR and AD-DR adjacent to the upper left side, the lower left side, the upper right side and the lower right side, respectively, of the target measurement area TG may not be considered as the adjacent measurement area.

Thereafter, the reference data and the measurement data of the adjacent measurement areas AD-U, AD-D, AD-L, AD-R, AD-UL, AD-DL, AD-UR and AD-DR adjacent to the target measurement area TG are acquired in step of S130.

Figure 3:
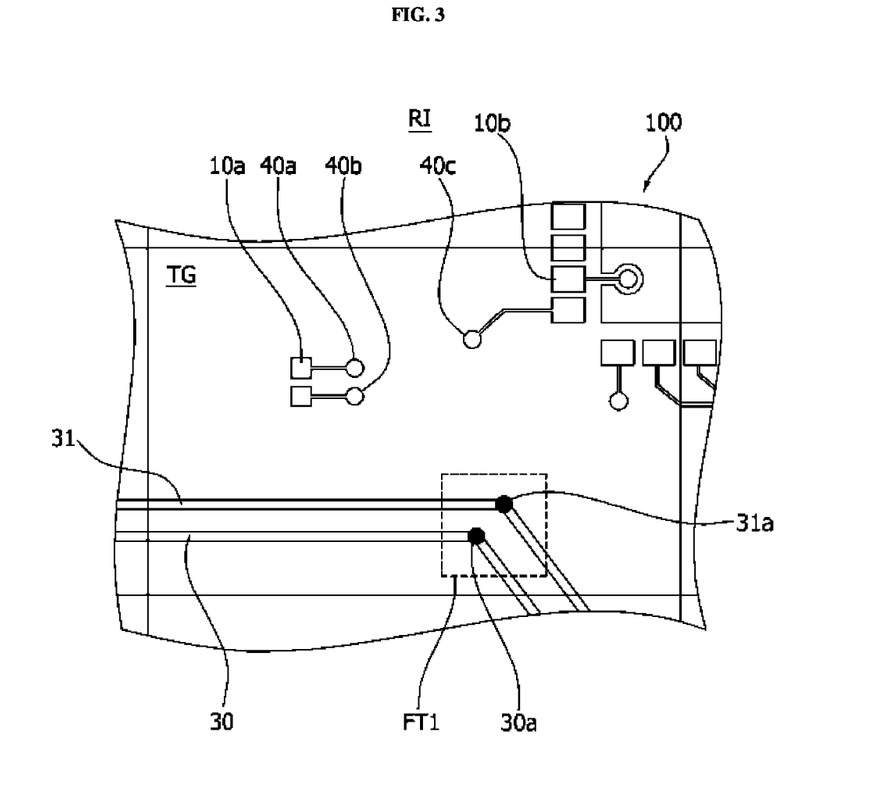
FIG. 3 is a plan view illustrating reference data in the inspection method shown in FIG. 1.

FIG. 3 is a plan view illustrating reference data in the inspection method shown in FIG. 1.

Referring to FIG. 3, the reference data RI, for example, may correspond to a theoretical plan view of the board 100.

In an exemplary embodiment, the reference data RI may be obtained from CAD information or gerber information in which a shape of the board is recorded. The CAD information or the gerber information may include design information of the board, and typically include configuration information of pads 10a and 10b, circuit patterns 30 and 31, hole patterns 40a, 40b and 40c, etc.

In another exemplary embodiment, the reference data RI may be acquired from learning information that is obtained in a learning mode. The learning mode may be realized by processes, for example, such as searching board information in a database, learning a bare board in case that the board information is not in the database, and storing the board information in the database after the board information is produced by learning the bare board. That is, in the learning mode, a bare board of a PCB is learned and design reference information of the PCB is acquired, and the reference data RI may be acquired by obtaining the learning information through the learning mode.

Figure 4:
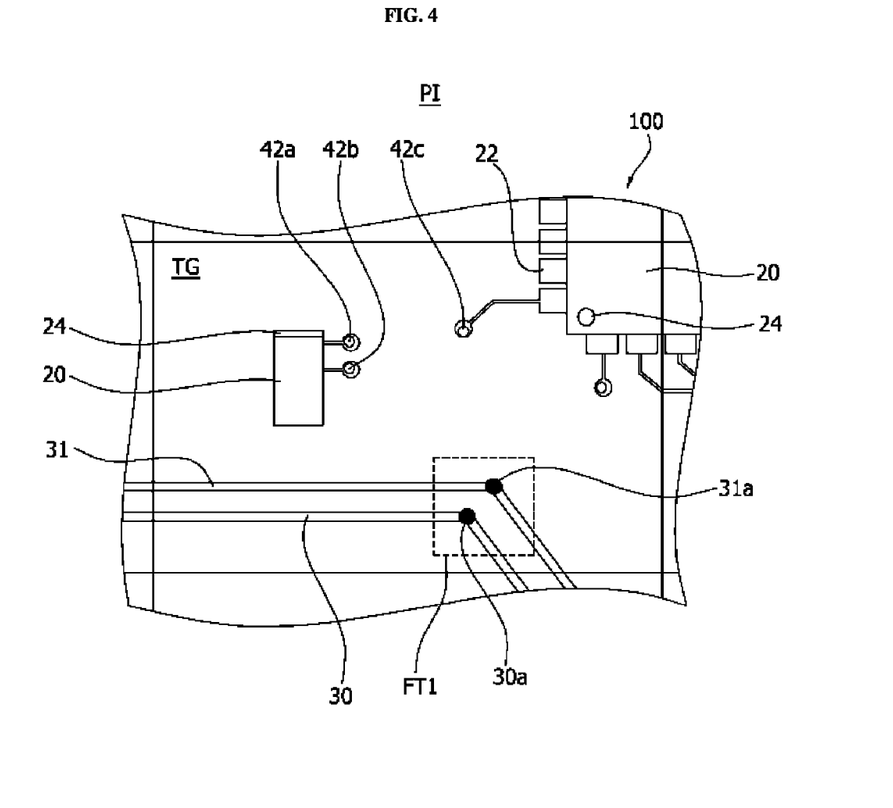
FIG. 4 is a plan view illustrating measurement data in the inspection method shown in FIG. 1.

FIG. 4 is a plan view illustrating measurement data in the inspection method shown in FIG. 1.

Referring to FIG. 4, the measurement data PI may be, for example, a real captured image for a PCB. For example, a component 20 mounted on the board 100, a terminal 22, a polar indication 24 formed at the component 20, circuit patterns 30 and 31, holes 42a, 42b and 42c, etc. may be shown in the measurement data PI.

The measurement data PI has, as shown in FIG. 4, the same image as the reference data RI shown in FIG. 3 except for additional elements such as the component 20. However, the measurement data PI is distorted in comparison with the reference data RI, due to warpage, contortion, etc. of the board 100.

In an exemplary embodiment, the measurement data PI may be acquired by providing light onto the target measurement area TG using the illumination section of the inspection apparatus, and capturing an image reflected by the provided light using a camera installed in the inspection apparatus. Alternatively, the measurement data PI may be acquired by projecting grating pattern light onto the target measurement area TG using a grating pattern projecting section of the inspection apparatus, and capturing an image reflected by the projected grating pattern light.

Referring to FIGS. 1 to 4, then, at least one feature object is extracted from the target measurement area TG and the adjacent measurement areas AD-U, AD-D, AD-L, AD-R, AD-UL, AD-DL, AD-UR and AD-DR in step of S140.

The feature object is used as a comparison reference to acquire a conversion relation between the reference data RI and the measurement data PI. That is, the conversion relation is defined by using a degree by which the feature object is changed between the reference data RI and the measurement data PI due to the distortion of the board 100.

The feature object may include an object having a specific shape, which is located at a predetermined coordinate in the reference data RI and the measurement data PI. For example, the feature object may include a hole pattern, a corner portion (refer to 30a and 31a in FIGS. 3 and 4) of a bent circuit pattern, etc. formed on the board 100, and a conversion relation, which will be described later, may be obtained by comparing the reference data RI and the measurement data PI with each other based on a coordinate of a central point of a hole pattern or a coordinate of a corner point of a corner point of a bent circuit pattern.

Alternatively, the feature object, as shown in FIGS. 3 and 4, may be defined as a feature block by a block unit. In case of defining the feature object as a feature block, since the reference data RI and the measurement data PI may be compared with each other based on various shapes included in the feature block, the reference data RI and the measurement data PI may be accurately compared with each other.

Since the feature object is used as a comparison reference to acquire a conversion relation between the reference data RI and the measurement data PI, it is desirable to accurately establish the feature object in the reference data RI and the measurement data PI. That is why an error may be incurred in comparing the reference data RI and the measurement data PI corresponding to the feature object with each other when the feature object is not accurately established in the reference data RI and the measurement data P. Thus, the feature object may be established so that misidentification probability is removed.

For the above accurate establishment, it may occur that no object or few objects selectable as the feature object exist in the target measurement area TG. Thus, in order to secure sufficient feature objects, the feature objects may be extracted from the adjacent measurement areas AD-U, AD-D, AD-L, AD-R, AD-UL, AD-DL, AD-UR and AD-DR adjacent to the target measurement area TG.

After establishing the feature objects for the plurality of measurement areas in advance, some of the established feature objects may be extracted in the present step. Alternatively, the feature objects may be simultaneously established in and extracted from the target measurement area TG and the adjacent measurement areas AD-U, AD-D, AD-L, AD-R, AD-UL, AD-DL, AD-UR and AD-DR in the present step.

The feature objects may be established based on the reference data RI, and also based on the measurement data PI.

In an exemplary embodiment, when at least one feature object is extracted from the target measurement area TG and the adjacent measurement areas AD-U, AD-D, AD-L, AD-R, AD-UL, AD-DL, AD-UR and AD-DR in step of S140, one or more adjacent measurement areas for extracting the feature object may be selected from the adjacent measurement areas AD-U, AD-D, AD-L, AD-R, AD-UL, AD-DL, AD-UR and AD-DR.

In another exemplary embodiment, before extracting the feature object in step of S140, after the feature object for each measurement area is established in advance, it is checked whether the number of the established feature object for each measurement areas is smaller than a reference number or not. Then, in case that there exists a measurement area in which the number of the feature object is smaller than the reference number, an adjacent measurement area for extracting the feature object may be selected for such a measurement area in advance.

Figure 5:
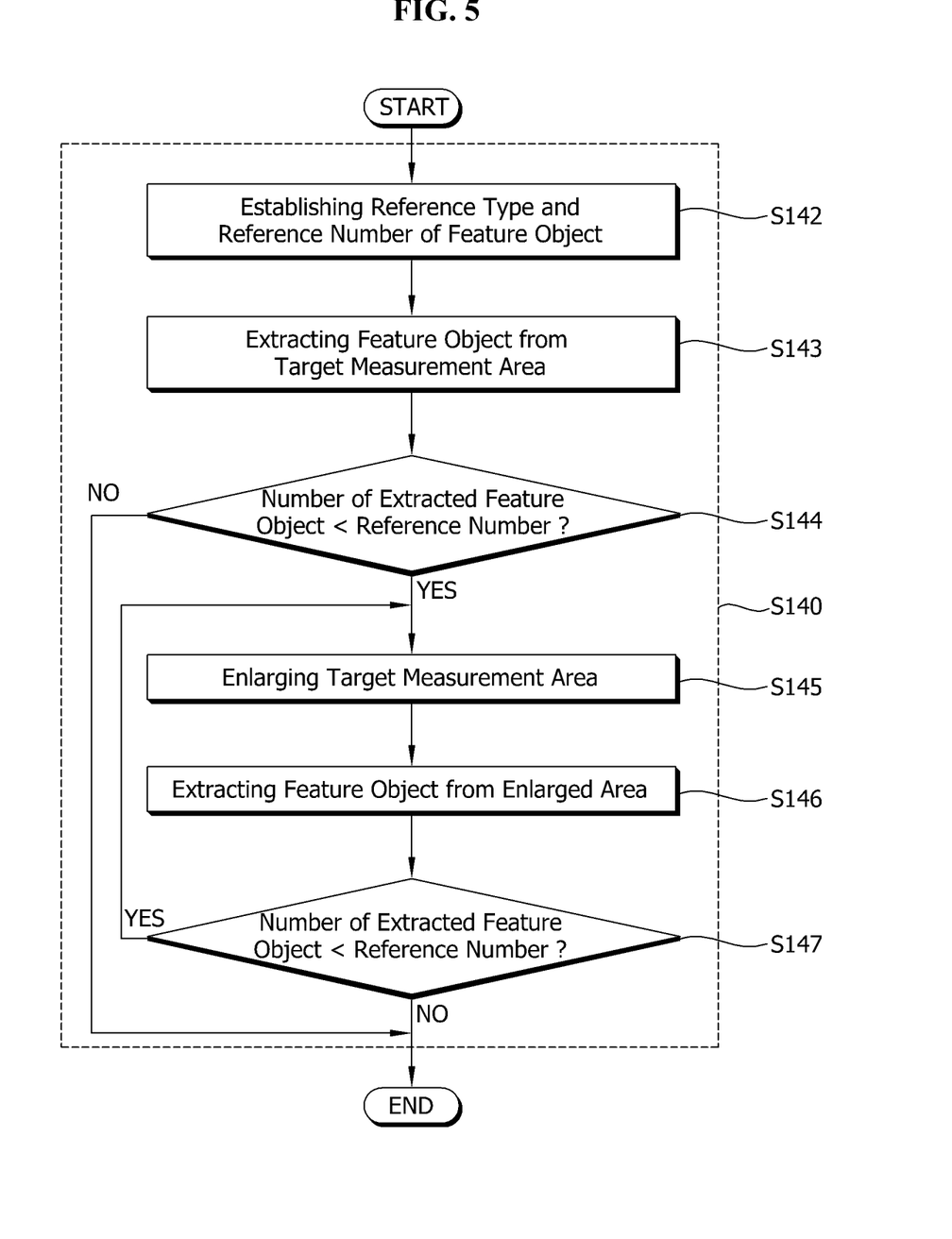
FIG. 5 is a flow chart illustrating an exemplary embodiment for a method of extracting a feature object in the inspection method shown in FIG. 1.
Figure 6:
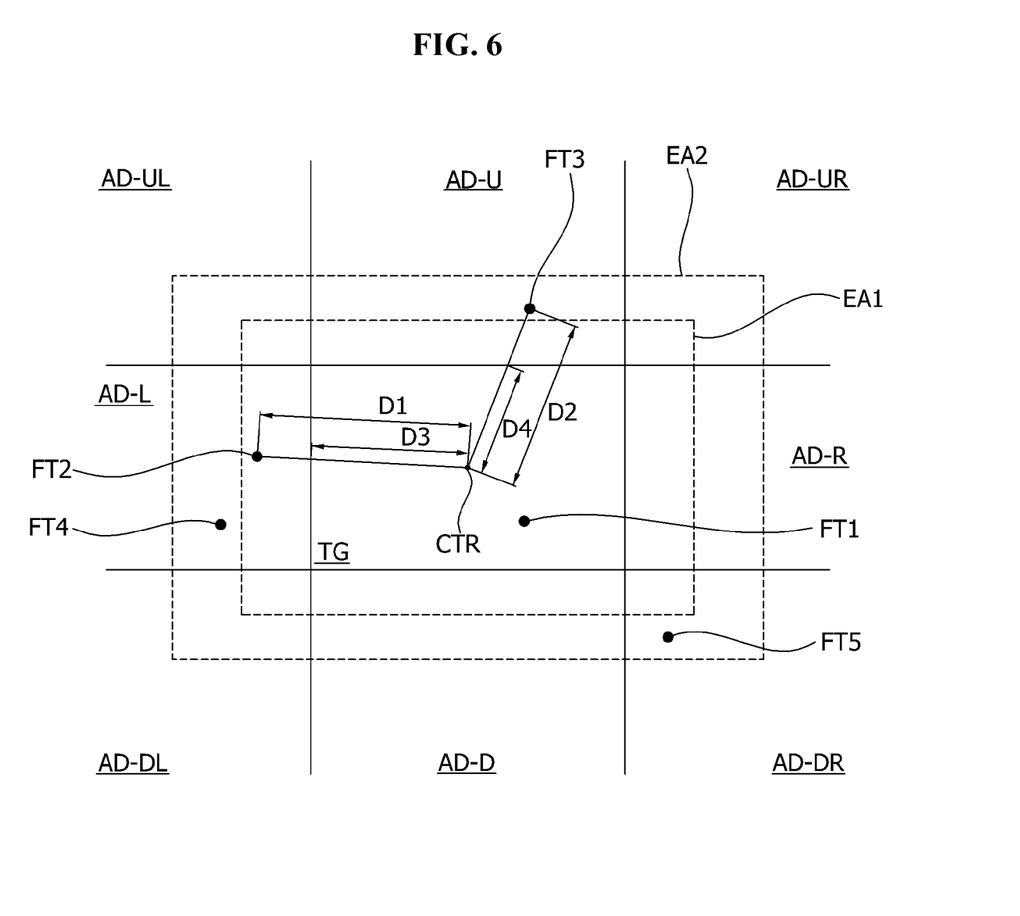
FIG. 6 is a schematic plan view illustrating a method of extracting a feature object in FIG. 1.

FIG. 5 is a flow chart illustrating an exemplary embodiment for a method of extracting a feature object in the inspection method shown in FIG. 1. FIG. 6 is a schematic plan view illustrating a method of extracting a feature object in FIG. 1.

Referring to FIGS. 5 and 6, first, a reference type for using the feature object and a reference number thereof are established in step of S142.

For example, the reference type may be established as two bent patterns substantially parallel with each other in a feature block, such as a first feature object FT shown in FIGS. 3 and 4, and the reference number may be established as three, four, etc. corresponding to the number that is capable of defining a conversion relation according to a distortion degree.

Then, the feature object corresponding to the reference type is extracted from the target measurement area TG in step of S143.

Thereafter, the number of the feature object extracted from the target measurement area TG is compared with the reference number in step of S144.

In case that the number of the feature object extracted from the target measurement area TG is smaller than the reference number, the target measurement area TG is enlarged by a predetermined area in step of S145, and otherwise, since the desired number of the feature object has been obtained, the step of extracting the feature object is terminated.

For example, in case that the reference number is four, and there exists only a first feature object FT1 serving as the feature object in the target measurement area TG as shown in FIG. 6, since the number of the feature object extracted from the target measurement area TG is one, which is smaller than the reference number, four, the target measurement area TG is enlarged by a predetermined area.

The enlargement method may include, for example, a proportional enlargement for each boundary line of the target measurement area TG. Alternatively, the target measurement area TG may be enlarged so that distances from the boundary lines of the target measurement area TG are the same.

Then, the feature object corresponding to the reference type is extracted from the enlarged area corresponding to the adjacent measurement areas AD-U, AD-D, AD-L, AD-R, AD-UL, AD-DL, AD-UR and AD-DR in step of S146.

For example, as shown in FIG. 6, since a second feature object FT2 corresponding to the reference type exists in a first enlarged area EA1, the second feature object FT2 is extracted as the feature object.

Thereafter, the number of the extracted feature object and the reference number are compared with each other in step of S147.

In case that the number of the extracted feature object is smaller than the reference number, the step of enlarging the target measurement area by a predetermined area in step of S145 and the next step are repeated, and otherwise, since the desired number of the feature object has been obtained, the step of extracting the feature object is terminated.

For example, in case that the reference number is four, and there exists a first feature object FT1 and a second feature object FT2 serving as the feature object in the target measurement area TG and the first enlarged area EA1 as shown in FIG. 6, since the number of the feature object extracted from the target measurement area TG and the first enlarged area EA1 is two, which is smaller than the reference number, four, the target measurement area TG is enlarged by a predetermined area in step of S145, the feature object is additionally extracted.

In case that the number of the feature object exceeds the reference number, the feature object corresponding to the excess number may be excluded from the extraction. In this case, the feature objects may be evenly extracted within the scope of the reference number.

For example, in case that a third feature object FT3, a fourth feature object FT4 and a fifth feature object FT5 are extractable as the feature object corresponding to the reference type from a second enlarged area EA2 corresponding to the adjacent measurement areas AD-U, AD-D, AD-L, AD-R, AD-UL, AD-DL, AD-UR and AD-DR, since the number of the feature object is five, which exceeds the reference number, four, any one of the third feature object FT3, the fourth feature object FT4 and the fifth feature object FT5 may be excluded from the extraction of the feature object. Since the fourth feature object FT4 belongs to the same area as the second feature object FT2, the adjacent measurement area AD-L, the fourth feature object FT4 may be excluded from the extraction of the feature object so as to evenly extract the feature objects. Thus, the feature objects corresponding to the reference number, four are the first feature object FT1, the second feature object FT2, the third feature object FT3, and the fifth feature object FT5.

The feature object may be extracted from the adjacent measurement area in which measurement is completed, so as to use previously acquired measurement data.

Figure 7:
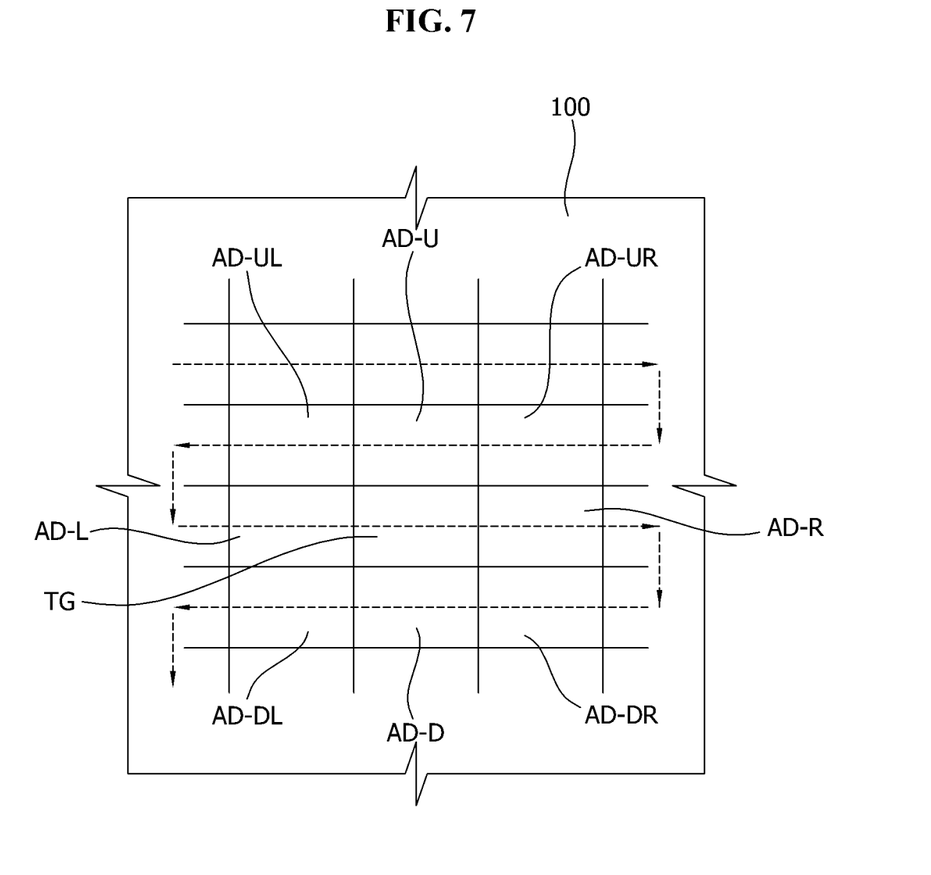
FIG. 7 is a schematic plan view illustrating another exemplary embodiment for a method of extracting a feature object in FIG. 1.

FIG. 7 is a schematic plan view illustrating another exemplary embodiment for a method of extracting a feature object in FIG. 1.

Referring to FIG. 7, the feature object the feature object may be extracted from a specific adjacent measurement area in which the measurement data is acquired before the measurement data of the target measurement area TG is acquired.

For example, as shown in FIG. 7, when measurement data of measurement areas are acquired in an order along an arrow direction, the feature object may be extracted from specific adjacent measurement areas AD-UR, AD-U, AD-UL and AD-L in which the measurement data is measured before the measurement data of the target measurement area TG is measured.

Since the feature objects existing in the adjacent measurement areas AD-U, AD-D, AD-L, AD-R, AD-UL, AD-DL, AD-UR and AD-DR located outside the target measurement area TG for setting an inspection area are used for acquiring a distortion degree, which will be described later, and distances of the feature objects, which are distant from the target measurement area TG, are different from each other, weighted values according to a regular rule may be given to the feature objects.

In an exemplary embodiment, a greater weighted value may be given to the feature object as a distance between the feature object and the target measurement area TG is nearer.

For example, the greatest weighted value is given to the feature object existing in the target measurement area TG, and in case of the feature object existing in the adjacent measurement areas AD-U, AD-D, AD-L, AD-R, AD-UL, AD-DL, AD-UR and AD-DR, a greater weighted value may be given to the feature object as a distance between the feature object and the target measurement area TG is nearer.

For example, the greatest weighted value is given to the first feature object FT1 existing in the target measurement area TG, the next greatest weighted value is given to the second feature object FT2, and the smallest weighted value is given to the third feature object FT3 and the fifth feature object FT5. In addition, in case of the second feature object FT2, third feature object FT3 and the fifth feature object FT5, the weighted value may be given proportional to a distance from the target measurement area TG. The distance may be measured from at least one of a boundary line of the target measurement area TG, or a central point CTR of the target measurement area TG. In addition, the distance may be measured from a central point of the measurement target formed in the target measurement area TG.

In case that the distance is measured from the central point CTR of the target measurement area TG or the central point of the measurement target, the weighted value may be given to the first feature object FT1 existing in the target measurement area TG according to the distance from the central point CTR of the target measurement area TG or the central point of the measurement target.

In addition, in case that the distance is measured from the central point CTR of the target measurement area TG or the central point of the measurement target, the distance may indicate an enlargement proportion when the shape of the target measurement area TG is proportionally enlarged. For example, in case that the distance is measured from the central point CTR of the target measurement area TG, as shown in FIG. 6, a first distance D1 from the central point CTR to the second feature object FT2 is longer than a second distance D2 from the central point CTR to the fourth feature object FT4. However, as for the enlargement proportion when the shape of the target measurement area TG is proportionally enlarged, since a first enlargement proportion of the second feature object FT2, D1/D3 is smaller than a second enlargement proportion of the fourth feature object FT4, D2/D4, the second feature object FT2 is considered to have a distance shorter than that of the fourth feature object FT4.

A distortion degree between the reference data RI and the measurement data PI, which will be described later, may be acquired based on the weighted values.

Independently from the weighted value or with the weighted value, scores according to a regular rule may be given to the feature objects.

For example, a greater score is given to the feature object as a shape difference between the reference data and the measurement data corresponding to the feature object is smaller, and the feature object having a greater score is extracted to acquire the distortion degree.

Referring again to FIGS. 1 and 2, thereafter, a distortion degree is acquired by comparing reference data RI and measurement data PI corresponding to the feature object with each other in step of S150.

The distortion degree may be expressed as a conversion relation between the reference data RI and the measurement data PI, and the conversion relation may include a quantified conversion formula between the reference data RI and the measurement data PI.

The measurement data PI is distorted due to warpage, contortion, etc. of the board in comparison with the reference data RI corresponding to theoretical reference information. The conversion formula corresponds to a formula converting the reference data RI and the measurement data PI into each other so as to express a degree of the distortion, i.e., the distortion degree. The quantified conversion formula may be determined by using at least one of a location change, a slope change, a size change and a transformation degree, which are acquired by comparing the reference data RI and the measurement data PI corresponding to the feature object with each other.

For example, the conversion formula may be acquired by using Equation 1.

$$P_{CAD} f(tm) = P_{real}  \quad \text{Equation 1}$$

In Equation 1, $P_{CAD}$ is a coordinate of a target in CAD information or gerber information, i.e., a coordinate in the reference data RI, f(tm) corresponds to the conversion formula serving as a conversion matrix or a transfer matrix, and $P_{real}$ is a coordinate of the target in the measurement data PI, which is acquired by a camera. When the theoretical coordinate $P_{CAD}$ in the reference data RI and the real coordinate $P_{real}$ in the measurement data PI are found, the conversion matrix may be known.

For example, the conversion matrix may include a coordinate conversion matrix according to an affine conversion or a perspective conversion, in which point-to-point relation is expressed as a first-order form in an n-dimensional space. In order to define the coordinate conversion matrix, the number of the feature objects may be properly established, for example, more than or equal to three in case of an affine conversion and more than or equal to four in case of a perspective conversion.

Then, the distortion degree is compensated for, to set an inspection area in the target measurement area in step of S160.

For example, the inspection area for inspecting the measurement target in the measurement area may be set by converting the measurement data PI by using conversion value of a degree of distortion in the measurement target, which is acquired by the conversion relation, or by applying an equation concerning the conversion relation to the reference data RI for conversion.

Since the distortion existing in the measurement data PI may be compensated for by using the conversion relation and comparing the measurement data PI with the reference data RI, the shape in the set inspection area may be more similar to a real shape for the board. The inspection area may be set for the entire area of the target measurement area TG, and may be set for only a predetermined area for which inspection is desired.

For example, after a predetermined area, for which inspection is desired, is selected, and an inspection area is set in the measurement data PI by using the conversion relation, various states such as a connection state of components may be inspected in the inspection area. In the inspection, the measurement data PI may be used, which is previously acquired in a step of acquiring measurement data PI for the target measurement area TG (step S130).

As described above, in case that there is no shape information or few shape information for establishing a feature object in the target measurement area on a board, a feature object is additionally established in an adjacent measurement area to thereby more correctly acquire a conversion relation between reference data and measurement data, and set an inspection area by compensating for distortion of measurement data with the conversion relation.

In addition, in case of establishing a feature block including a specific shape by a block unit as a feature object, since it may occur sometimes that there is insufficient shape information selectable as a feature object, a feature object in an adjacent measurement area may be used, as described above, to acquire the sufficient number of feature objects.

In addition, in case that weighted value is established for feature objects in a target measurement area and an adjacent measurement area, a conversion relation comparatively correct may be acquired. In addition, in case that feature objects are evenly established for a plurality of adjacent measurement areas, a conversion relation comparatively correct may be acquired.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An inspection method comprising:
setting a plurality of measurement areas on a board;
acquiring reference data and measurement data of at least one adjacent measurement area that is adjacent to a target measurement area for inspecting a measurement target, among the measurement areas;
extracting at least one feature object from the adjacent measurement area;
acquiring a distortion degree by comparing reference data and measurement data corresponding to the feature object with each other; and
compensating for the distortion degree to set an inspection area in the target measurement area.

2. The inspection method of claim 1, prior to extracting at least one feature object from the adjacent measurement area, further comprising:
establishing the feature object for each measurement area;
checking whether the number of the established feature object is smaller than a reference number or not, for each measurement area; and
selecting the adjacent measurement area for extracting the feature object for the measurement area in which the number of the established feature object is smaller than the reference number.

3. The inspection method of claim 1, wherein the feature object is extracted from a specific adjacent measurement area in which the measurement data is acquired before the measurement data of the target measurement area is acquired.

4. The inspection method of claim 1, wherein the extracted feature object is plural, and
wherein a greater score is given to the feature object as a shape difference between the reference data and the measurement data corresponding to the feature object is smaller, and the distortion degree is acquired by comparing the reference data and the measurement data corresponding to the feature object selected based on the score with each other.

5. The inspection method of claim 1, wherein the extracted feature object is plural, and
wherein a greater weighted value is given to the feature object as a distance between the feature object and the target measurement area is nearer, a greater score is given to the feature object as a shape difference between the reference data and the measurement data corresponding to the feature object is smaller, and the distortion degree is acquired by comparing the reference data and the measurement data corresponding to the feature object selected based on at least one of the weighted value and the score with each other.

6. The inspection method of claim 1, wherein the adjacent measurement area is plural, and the extracted feature object is plural, and
wherein the feature objects are evenly extracted for the plurality of adjacent measurement areas.

7. The inspection method of claim 1, wherein extracting at least one feature object in the adjacent measurement area comprises:
establishing a reference type and a reference number of the feature object; and
extracting the feature object corresponding to the reference type from the adjacent measurement area, in case that the number of the feature object extracted from the target measurement area is smaller than the reference number.

8. The inspection method of claim 7, wherein the adjacent measurement area is plural, and prior to extracting the feature object corresponding to the reference type from the adjacent measurement area, extracting at least one feature object from the adjacent measurement area further comprises selecting the adjacent measurement area for extracting the feature object among the plurality of adjacent measurement areas.

9. The inspection method of claim 1, wherein the extracted feature object is plural, and
wherein a greater weighted value is given to the feature object as a distance between the feature object and the target measurement area is nearer, and the distortion degree is acquired by comparing the reference data and the measurement data corresponding to the feature object selected based on the weighted value with each other.

10. The inspection method of claim 9, wherein the distance is measured from at least one of a boundary line of the target measurement area, a central point of the target measurement area and a central point of the measurement target.

11. The inspection method of claim 1, wherein extracting at least one feature object from the adjacent measurement area comprises:
establishing a reference type and a reference number of the feature object;
enlarging the target measurement area by a predetermined area;
extracting the feature object corresponding to the reference type in the enlarged area; and
repeating the step of enlarging the target measurement area by a predetermined area, and the step of extracting the feature object corresponding to the reference type in the enlarged area, in case that the number of the extracted feature object is smaller than the reference number.

12. The inspection method of claim 11, wherein enlarging the target measurement area by a predetermined area is performed by extracting the feature object corresponding to the reference type in an intersection area between the enlarged area and at least one selected adjacent measurement area.

13. The inspection method of claim 11, prior to enlarging the target measurement area by a predetermined area, further comprising extracting the feature object corresponding to the reference type in the target measurement area, and
enlarging the target measurement area by a predetermined area is performed, in case that the number of the feature object extracted from the target measurement area is smaller than the reference number.

14. An inspection method comprising:
setting a plurality of measurement areas on a board;
acquiring reference data and measurement data of at least one adjacent measurement area that is adjacent to a target measurement area for inspecting a measurement target, among the measurement areas;
extracting at least one feature block having a block unit from the adjacent measurement area;
acquiring a distortion degree by comparing reference data and measurement data corresponding to the feature block with each other; and
compensating for the distortion degree to set an inspection area in the target measurement area.

15. The inspection method of claim 14, wherein the extracted feature block is plural,
the distortion degree is acquired as a quantified conversion formula between the reference data and the measurement data, and
the quantified conversion formula is determined by using at least one of a location change, a slope change, a size change and a transformation degree, which are acquired by comparing the reference data and the measurement data corresponding to the plurality of feature objects with each other.

* * * * *